US00PP18106P2

(12) United States Plant Patent
Pieters

(10) Patent No.: US PP18,106 P2
(45) Date of Patent: Oct. 2, 2007

(54) ***CHRYSANTHEMUM* PLANT NAMED 'PPP MIL YL05'**

(50) Latin Name: *Chrysanthemum morifolium*
Varietal Denomination: PPP MIL YL05

(75) Inventor: Dirk Pieters, Oostnieuwkerke (BE)

(73) Assignee: Pieters Plant Production, Oostnieuwkerke (BE)

( * ) Notice: Subject to any disclaimer, the term of this patent is extended or adjusted under 35 U.S.C. 154(b) by 0 days.

(21) Appl. No.: 11/414,887

(22) Filed: Apr. 29, 2006

(51) Int. Cl.
*A01H 5/00* (2006.01)

(52) U.S. Cl. ..... Plt./289

(58) Field of Classification Search ..... Plt./289
See application file for complete search history.

*Primary Examiner*—Kent Bell
*Assistant Examiner*—June Hwu

(57) ABSTRACT

A new and distinct *Chrysanthemum* plant cultivar is disclosed, characterized by large decorative type inflorescences, consistent flowering response to short days, blooming consistently after 49 days of short day length, bright yellow ray florets, free branching habit, and a consistent natural season flowering habit during the first week of September.

1 Drawing Sheet

Latin name of the genus and species: *Chrysanthemum morifolium.*
Variety denomination: 'PPP MIL YL05'.

BACKGROUND OF THE INVENTION

The new cultivar 'PPP MIL YL05' is a product of an induced mutation of the parent *Chrysanthemum* plant variety 'GEDI THREE MIL' (U.S. Plant Pat. No. 16,843) using gamma ray treatment at a dose of 20 Gy. The new cultivar was discovered and selected by Dirk Pieters in September 2003 in Oostnieuwkerke, Belgium.

Asexual reproduction of the new cultivar 'PPP MIL YL05' by terminal cuttings and tissue culture was performed in Oostnieuwkerke, Belgium and Oxnard, Calif. and has shown that the unique features of this new cultivar are stable and reproduced true to type on successive generations.

SUMMARY OF THE INVENTION

The cultivar 'PPP MIL YL05' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP MIL YL05.' These characteristics in combination distinguish 'PPP MIL YL05' as a new and distinct *Chrysanthemum* cultivar:

1. Large bright yellow inflorescence;
2. Consistent flowering response to short days, blooming consistently after 49 days of short day length.
3. Free branching habit; and
4. Consistent natural season flowering habit during the first week of September.

Plants of the new cultivar 'PPP MIL YL05' are similar to plants of the parent variety, 'GEDI THREE MIL,' in most horticultural characteristics, however plants of the new cultivar 'PPP MIL YL05' are shorter but wider than the parent. Also, 'GEDI THREE MIL' has more inflorescences per lateral branch than the new cultivar 'PPP MIL YL05.' Finally, 'GEDI THREE MIL' has more ray florets than the new cultivar and 'PPP MIL YL05' has bright yellow ray florets compared to the yellow-white ray florets of the parent.

In comparison to the commercially available variety 'GEDI ONE CES' (U.S. Plant Pat. No. 13,797), 'PPP MIL YL05' is shorter and wider. Additionally, the new variety 'PPP MIL YL05' has smaller leaves. Further, the new variety 'PPP MIL YL05' has a smaller center with very little disc florets and has truer yellow ray florets than the comparable variety 'GEDI ONE CES.'

BRIEF DESCRIPTION OF THE PHOTOGRAPH

The accompanying photograph in FIG. 1 illustrates in full color a typical plant of 'PPP MIL YL05' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP MIL YL05' plants grown in Oxnard, Ventura County, Calif., during the months of May through September 2005. The growing temperature ranged from 12° C. to 15° C. at night to 12° C. to 20° C. during the day. Measurements and numerical values represent averages of typical flowering types.

Botanical classification: *Chrysanthemum morifolium* cultivar 'PPP MIL YL05.'
Commercial classification: Garden-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 22 cm.
Plant spread: Approximately 46 cm.
Growth rate: Moderate.
Branching characteristics: Free Branching.
Length of lateral branches: Approximately 18 cm.
Number of leaves per lateral branch: Approximately 32.
Age of plant described: Approximately 120 days.

FOLIAGE

Leaf:
*Arrangement.*—Alternate single.
*Average length.*—Approximately 4 cm.
*Average width.*—Approximately 3.3 cm.
*Shape of blade.*—Ovate.
*Apex.*—Acuminate.
*Base.*—Attenuate.
*Attachment.*—Stalked.
*Margin.*—Serrate.
*Texture of top surface.*—Lightly pubescent.
*Texture of bottom surface.*—Lightly pubescent.
*Leaf internode length.*—Approximately 1.8 cm.
*Color.*—Young foliage upper side: Near Green 137A. Young foliage under side: Near Green 138B. Mature foliage upper side: Near Green 137A. Mature foliage under side: Near Green 138B.
*Venation.*—Type: Palmately net. Venation color upper side: Near Green 138C. Venation color under side: Near Green 138C.
Petiole:
*Average length.*—Approximately 1.1 cm.
*Color.*—Near Green 138C.
*Diameter.*—Approximately 0.2 cm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately first week in September.
*Number of inflorescences per lateral branch.*—Approximately 12.
*Inflorescence diameter.*—Approximately 5.9 cm.
*Inflorescence depth.*—Approximately 1.8 cm.
*Inflorescence longevity on plant.*—Approximately 28 to 32 days.
*Persistence.*—Persistent.
Ray florets:
*Appearance.*—Matte.
*Texture.*—Smooth.
*Average number of ray florets per inflorescence.*—172.
*Shape.*—Oblanceolate.
*Aspect.*—Flat.
*Margin.*—Entire.
*Apex.*—Obtuse.
*Length.*—Approximately 1.7 cm.
*Width.*—Approximately 0.6 cm.
*Color.*—Upper surface at first opening: Near Yellow 8A. Upper surface at maturity: Near Yellow 9A. Upper surface at fading: Near Yellow 10A. Under surface at first opening: Near Yellow 8C. Under surface at maturity: Near Yellow 10C. Under surface at fading: Near Yellow 10D.
Disc florets:
*Appearance.*—Shiny.
*Texture.*—Smooth.
*Average number of florets per disc.*—Approximately 3.
*Shape.*—Cylindric.
*Apex.*—Obtuse.
*Average length.*—Approximately 0.3 cm.
*Average width.*—Approximately 0.1 cm.
*Color.*—At first opening: Near Yellow 13A. At maturity: Near Yellow 13A. At fading: Near Yellow 13C.
Peduncle:
*Length.*—At terminal end (shortest): Approximately 3.5 cm. At lateral end (longest): Approximately 4 cm.
*Angle to stem.*—Acute.
*Strength.*—Moderate.
*Color.*—Near.
*Habit.*—Upright.
*Diameter.*—Approximately 0.1 cm.
*Surface texture.*—Lightly pubescent.
Inflorescence bud:
*Length.*—Approximately 0.4 cm.
*Diameter.*—Approximately 0.8 cm.
*Form.*—Globular.
*Color.*—Near Yellow-Green 144C.
Involucral bracts (phyllaries):
*Appearance.*—Matte.
*Texture.*—Lightly pubescent.
*Number.*—Approximately 20.
*Shape.*—Ovate.
*Margin.*—Entire.
*Apex.*—Acute.
*Length.*—Approximately 0.8 cm.
*Width.*—Approximately 0.2 cm.
*Color.*—Upper side: Near Green 138A. Under side: Near Green 143A.

REPRODUCTIVE ORGANS

Ray florets:
*Number of pistils per floret.*—1.
*Stigma shape.*—2 branched.
*Stigma color.*—Near Yellow 9A.
*Style color.*—Near Green-Yellow 1B.
*Style length.*—Approximately 0.3 cm.
*Stamens.*—Absent.
Disc florets:
*Number of pistils per floret.*—1.
*Stigma shape.*—Cylindric.
*Stigma color.*—Near Yellow 13A.
*Style length.*—Approximately 0.1 cm.
*Style color.*—Near Green-Yellow 1D.
*Number of stamens per floret.*—Approximately 5.
*Anther shape.*—Tubular.
*Anther color.*—Near Green-Yellow 1B.
*Pollen color.*—Near Yellow 13A.

OTHER CHARACTERISTICS

Disease resistance: Neither resistance nor susceptibility to diseases or pests has been observed in this variety.
Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP MIL YL05' as herein illustrated and described.

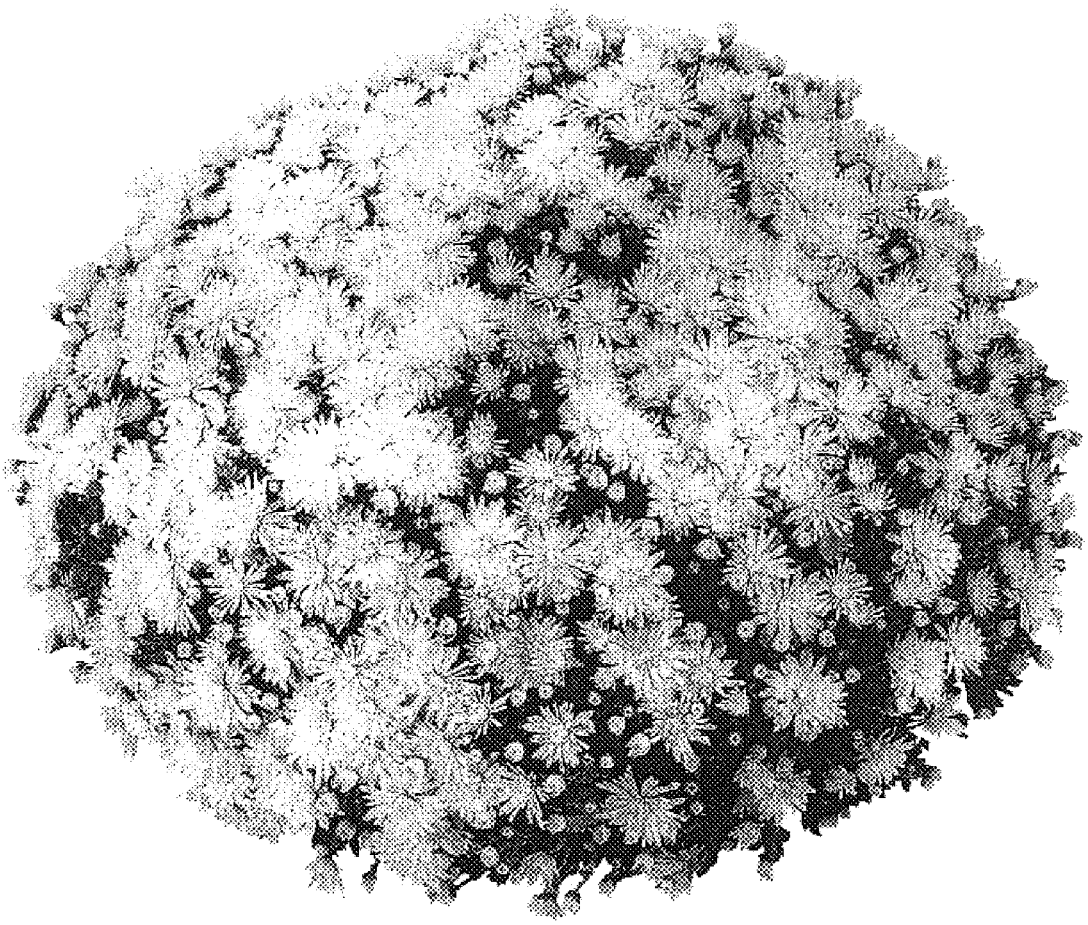

* * * * *